US007085804B2

(12) United States Patent
Nolte

(10) Patent No.: US 7,085,804 B2
(45) Date of Patent: Aug. 1, 2006

(54) METHOD FOR PROCESSING OBJECTS OF A STANDARDIZED COMMUNICATION PROTOCOL

(75) Inventor: Björn Nolte, Nürnberg (DE)

(73) Assignee: Siemens Aktiengesellschaft, Munich (DE)

( * ) Notice: Subject to any disclaimer, the term of this patent is extended or adjusted under 35 U.S.C. 154(b) by 785 days.

(21) Appl. No.: 10/105,585

(22) Filed: Mar. 25, 2002

(65) Prior Publication Data

US 2002/0146159 A1 Oct. 10, 2002

(30) Foreign Application Priority Data

Apr. 9, 2001 (DE) .................. 101 17 685

(51) Int. Cl.
*G06F 15/16* (2006.01)
*G06F 7/00* (2006.01)
*G06F 12/10* (2006.01)
*G06F 5/02* (2006.01)
*G06K 9/36* (2006.01)
*G06K 9/46* (2006.01)
*G09G 5/00* (2006.01)

(52) U.S. Cl. .................. 709/201; 709/204; 709/230; 709/246; 707/101; 707/103 R; 382/232; 345/3.2; 345/3.3; 345/569; 345/600

(58) Field of Classification Search ............. 709/201, 709/204, 246, 230; 707/103 R; 717/116, 717/16; 719/315, 332; 715/764; 382/232; 345/3.2, 3.3, 569, 600

See application file for complete search history.

(56) References Cited

U.S. PATENT DOCUMENTS

| 5,835,735 | A | * | 11/1998 | Mason et al. ............... 710/107 |
| 5,897,642 | A | * | 4/1999 | Capossela et al. .......... 707/203 |
| 5,956,513 | A | * | 9/1999 | McLain, Jr. ................ 717/142 |
| 6,049,822 | A | * | 4/2000 | Mittal ........................ 709/217 |
| 6,055,522 | A | * | 4/2000 | Krishna et al. ............. 715/517 |
| 6,094,684 | A | * | 7/2000 | Pallmann .................... 709/227 |
| 6,490,603 | B1 | * | 12/2002 | Keenan et al. ............. 715/513 |
| 6,934,698 | B1 | * | 8/2005 | Judd et al. .................... 707/1 |

OTHER PUBLICATIONS

MGJM Gerritsen et al., "General DICOM Pacs Server for Echocardiography Images", Computers in Cardiology 1999; 26:pp.431-434.*

RI Kitney et al., "An Object Oriented Multi-Modality Display and Analysis System Incorporating DICOM3", Computers in Cardiology 1994, pp. 181-183.*

RI Kitney et al., "A Comprehensive Web-Based Patient Information Enviornment", 2001, IEEE, 2001 Proceedings of the 23rd Annual EMBS International Conference, Oct. 25-28, Istanbul, Turkey, pp. 3584-3585.*

* cited by examiner

*Primary Examiner*—Saleh Najjar
*Assistant Examiner*—Michael Y. Won
(74) *Attorney, Agent, or Firm*—Schiff Hardin LLP

(57) ABSTRACT

In a method for processing objects of a standardized communication protocol for image and data exchange between devices via a communication network by means of processing devices, the objects are converted with a conversion routine into a pure text file (plain text), can be processed in a simple command language and are subsequently converted back into the objects.

6 Claims, 2 Drawing Sheets

METHOD FOR PROCESSING OBJECTS OF A STANDARDIZED COMMUNICATION PROTOCOL

BACKGROUND OF THE INVENTION

1. Field of the Invention

The present invention is directed to a method for processing objects of a standardized communication protocol for image and data exchange between devices via a communication network by means of processing devices. This image and data exchange can ensue as communication between medical devices with the communication protocol "Digital Imaging and Communication in Medicine" (DICOM).

2. Description of the Prior Art

The book "Bildgebende Systeme für die medizinische Diagnostik", edited by H. Morneburg, 3rd edition, 1995, pages 684ff, discloses medical system architectures, referred to as picture archival and communication systems (PACS), image viewing and image processing stations. These image processing stations, referred to as work stations, are connected to one another via an image communication network and to the remaining medical devices therein for calling patient data and images generated by imaging modalities.

This communication between medical systems and devices of different manufacturers via such an image communication network has become extremely important. The driving forces are cost reduction, quality enhancement and the ability to track and document medical information. In recent years, the medical communication standard DICOM 3.0 described in the aforementioned book on page 686 has become mature and widespread for manufacturers of medical devices and systems in order to send and receive digital images such as, for example, magnetic resonance, x-ray and ultrasound images.

New types of DICOM objects are continuously being added to the standard, and the standard itself is periodically reworked.

For example, every medical system and device that sends and receives DICOM messages has the following features:

1. The messages contain a block or a plurality of blocks of information.
2. Each block contains one or more information object descriptors (IOD).
3. Each IOD contains one or more information entities (IE).
4. Each IE contains one or more modules.
5. Each module contains one or more elements.
6. Elements can be simple elements or elements grouped in a container (sequence (SQ)).
7. SQs can contain simple elements or interleaved SQs of an arbitrary depth.

Simple elements are the smallest building blocks in DICOM. They are identifiable on the basis of a unique or (unambiguous) identification feature, what is referred to as an attribute tag.

Further, DICOM determines limitations of the messages: IODs have a one-time type identifier and a one-time event identifier. Newly developed IOD types are added to the standard. The IODs specify which modules must or can be contained in them. There is a global, expandable and overlapping set of modules from which the developers of the standard can select. A module specifies for each of its elements whether it can be empty or can have a zero value or can be omitted altogether. Dependencies between the elements within the modules exist. Mutual exclusions or inclusions are not unusual. Elements are also limited by virtue of a type defined in a type lexicon. Common types are coded strings or integer values. The standard also defines the multiplicity of the element values.

SUMMARY OF THE INVENTION

An object of the present invention is to provide a method of the type initially described that makes it possible to edit DICOM objects in a simple way and to construct artificial DICOM objects in order to be able to easily test medical systems or devices with new DICOM objects or in order to be able to easily test the readiness of the systems or devices with respect to modified or invalid DICOM objects.

This object is inventively achieved in a method wherein the objects are converted with a conversion routine into a pure text file (plain text), can be processed in a simple command language and are subsequently converted back into the objects, with the communication protocol being the medical communication protocol DICOM, and the objects of the communication protocol being DICOM objects, and wherein the conversion routine generates a respective binary file per tag with binary data in addition to the text file from the DICOM objects, and employs the binary files for tags with binary data in the re-conversion. Flexible editing, scripting and interactive communication possibilities in DICOM thus are obtained. As a result of the inventive method, an object can be optimally presented, for example an MR image can be edited in a simple way. By using a minimal language for describing each DICOM object to be represented, the inventive requirement for easy constructability is optimally met.

A tag with binary data can be a tag from the family OB, OW, OL, FL and/or FD tags that are converted into respective binary files, and the binary files for the OB, OW, OL, FL and/or FD tags are employed in the re-conversion.

An especially simple command language is obtained by setting a value from a string for processing the objects in the text file with a command s, setting a value from a binary file with a command f, opening a sequence of identification features (TAGs) with a command o and/or closing a sequence of TAGs with a command q. The command sequence can be ended with a command q.

It has proven advantageous when DICOM images are converted with a CDF conversion routine into a .cdf file as the pure text file and a respective binary file per OB, OW and OL tag. This allows the images to be processed in a cdf command language and subsequently converted back into the DICOM images.

DESCRIPTION OF THE PREFERRED EMBODIMENTS

Figure 1:
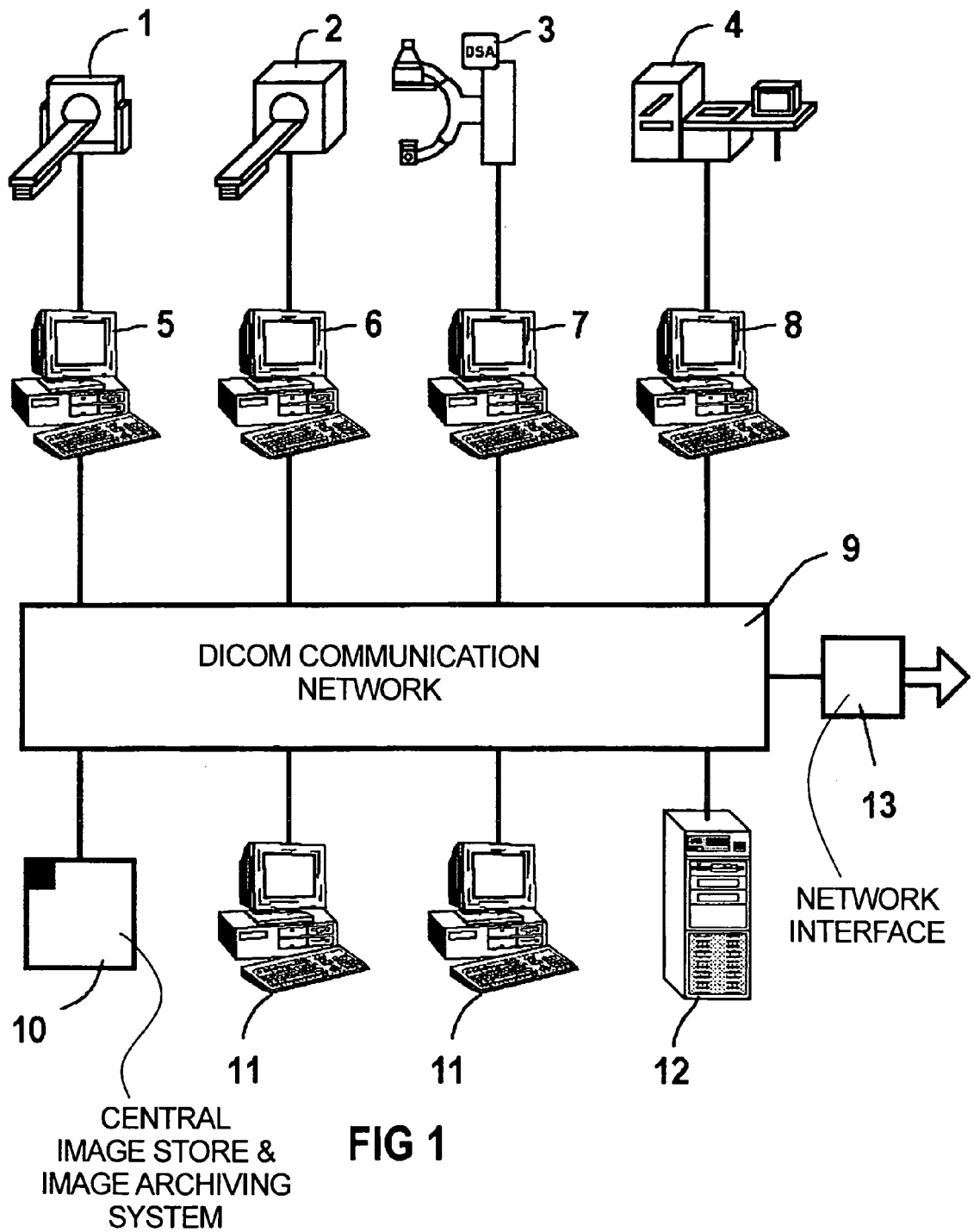
FIG. 1 illustrates an example of a system architecture of a hospital network.

FIG. 1 shows the system architecture of a hospital network as an example. The modalities 1 through 4 serve for acquiring medical images (image-generating systems) for example, a CT unit 1 for computed tomography, an MR unit 2 for magnetic resonance, a DSA unit 3 for digital subtraction angiography and an x-ray unit 4 for digital radiography. Control panels 5 through 8 of the modalities or workstations are connected to these modalities 1 through 4, the acquired medical images being processed and being able to be locally stored therewith. Patient data belonging to the images can also be entered.

The control panels 5 through 8 are connected to a communication network 9 as a LAN/WAN backbone for the distribution of the generated images and for communication. Thus, for example, the image is generated in the modalities 1 through 4 and the images further processed in the control panels 5 through 8 can be deposited in the central image store and image archiving system 10 or can be forwarded to other workstations.

Further viewing workstations 11 as diagnostic consoles are connected to the communication network 9, having local image stores. Such a viewing workstation 11 is, for example, a very fast mini-computer on the basis of one or more fast processors. The acquired images that are deposited in the image archiving system 10 can be subsequently called in the viewing workstations such as a workstation 11 for diagnosis and can be deposited in the local image store, from which they are immediately available to the diagnostician working at the viewing workstation 11.

Further, servers 12, for example patient data servers (PDS), file servers, program servers, EPR servers and/or RIS servers, are connected to the communication network 9 for communication with other components 5 through 8, 11 and 13 via TCP/IP protocols.

The image and data exchange via the communication network 9 thereby ensues according to the DICOM standard, a standard for the transmission of images and other medical information between computers, so that digital communication is possible between diagnostic and therapy devices of different manufacturers. A network interface 13 can be connected to the communication network 9, the internal communication network 9 being connected via the network interface 13 to a global data network, for example the worldwide web, so that the standardized data can be exchanged worldwide with different networks.

Figure 2:
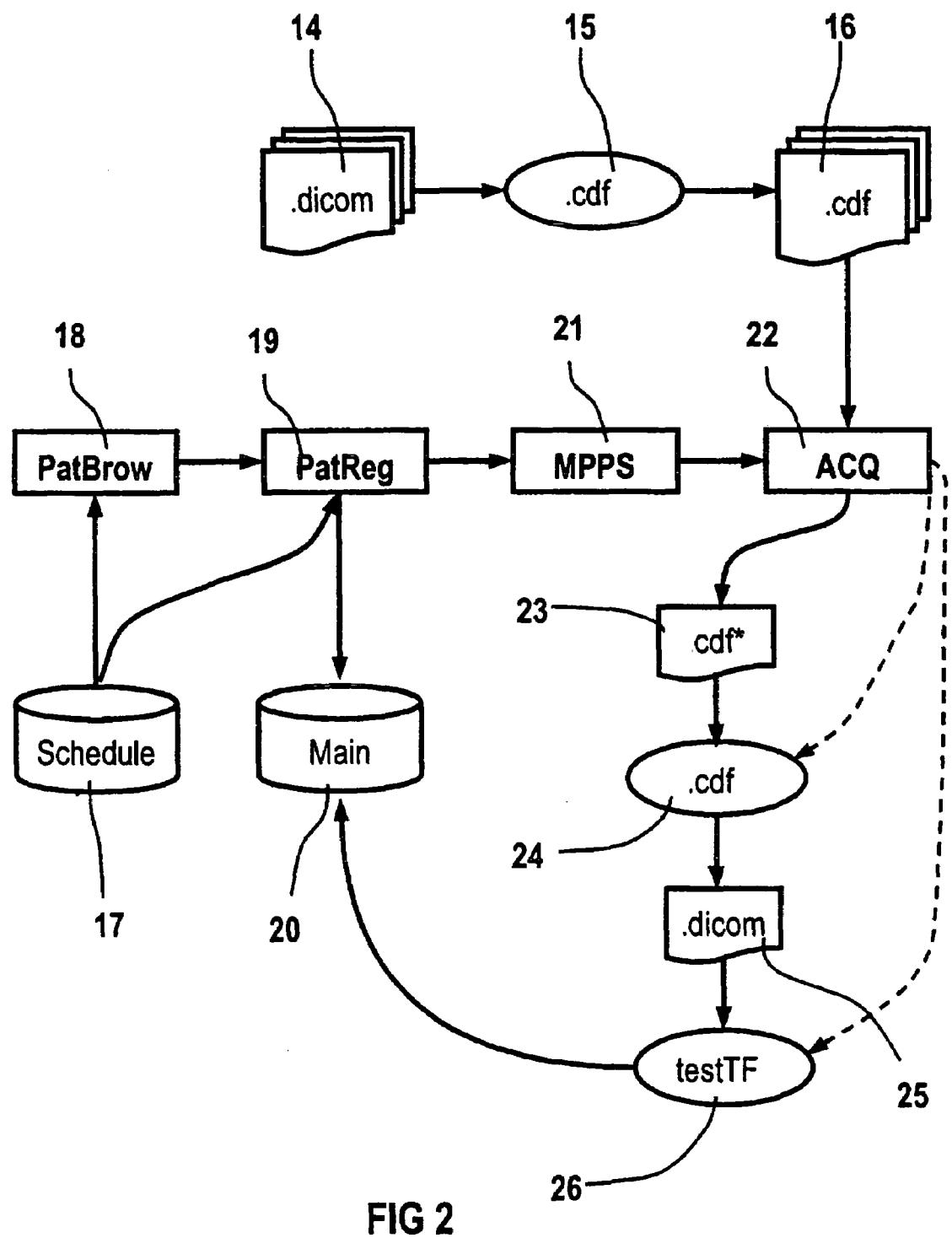
FIG. 2 shows a simulation concept for MR for explaining the inventive method.

FIG. 2 shows a simulation concept for MR, wherein objects in plain text (DICOM objects) for example MR images, from a DICOM data bank 14 are generated with a CDF conversion routine 15 (create DICOM file), said objects being stored in a CDF data bank 16 for processing. A work list schedule from a deadline data bank 17 is selected and displayed by a patient browser 18, a patient being selected therefrom and being transferred into the patient register 19 by pressing an examination button. The data of the patient are thereby read out from the deadline databank 17. Newly generated objects or copied objects are deposited in a main databank 20. An MPPS server 21 (Modality Performed Procedure Step) is informed of this. Subsequently, the acquisition 22 (ACQ) is started. Required images converted by the CDF conversion routine 15, what are referred to as .cdf images, are thereby readout from the CDF databank 16. For example, the current patient data are linked into these .cdf images and are stored in a .cdf* file 23. After calling the program .cdf.exe 24, the .cdf* files 23 are converted into .dicom files 25. By starting the test TF program 26, the .dicom file 25 can be imported to the main databank 20 and stored.

This DICOM editing service, as an Internet/Intranet service, thus makes it possible to convert DICOM images into plane text with a conversion routine 15. After the text representation of the images has been edited with a CDF command language, the DICOM editing service converts the plane text back into a DICOM image.

The DICOM editing service has the following properties:
It understands the newest MedCom DICOM implementation.
It works with interleaved DICOM sequences.
It understands private groupings.
It comprises a simple (short) but strong command language for maximum editing freedom.
It enables the creation of non-conforming or entirely artificial DICOM images.
The DICOM editing service is a WEB interface, i.e. it requires no software or software administration on client devices.

The inventive DICOM editing service enables simple uploading and downloading of the files from the server. The files sent to the server (upload) are converted if possible or, respectively, necessary. After the downloading, the files can be edited on the local device with any preferred text editor.
When the file loaded from the server ends with a ".dicom", the service generates a corresponding ".cdf" file (create dicom file) and a respective binary file per OB,
OW and OL tag.
with
OB=other byte (from the DICOM Standard), an 8-bit data type,
OW=Other word (from DICOM standard), a 16-bit data type, and
OL=Other long (from DICOM standard), a 32-bit data type for storing any data defined in DICOM.
When the file ends with ".cdf", the service generates a corresponding DICOM image. The binary files for OB, OW and OL tags must be available on the server.
Each file having a different extension is loaded without further actions. This possibility can be employed for editing the OB, OW and OL files.

Uploaded and generated files are found with a link onto these files in the server. Any file can be brought back to the PC by clicking onto the link. After the local editing of the file, this can be loaded back onto the server for further processing.

Inventively, the cdf language (cdf=create dicom file) is a simple command language, whereby only a single letter determines the desired command:
with the command s (setContentFromString), a value is set from a string,
with the command f (setContentFromFile), a value from a binary file is set,
the command o (openSQ) opens a sequence of tags,
the command c (closeSQ) closes a sequence of tags, when a line begins with #, it is a commentary,
no further commands are displayed with the optional command q.

An exemplary embodiment is set forth in Appendix 2.

The present invention recognizes and separates the dual nature of standard, the limitation part and the structural part of DICOM. The standard is also complicated by irregularities such as, for example, regressive nesting of SQs, empty SQs and elements privately defined by the manufacturer.

The method of the invention merely requires a minimum language in order to describe the structure at every possible DICOM message. It is composed only of four basic language elements [o, c, s, f]: openSQ, closeSQ, setContentFromString and setContentFromFile. Each language feature or each command takes a tag and, if required, a value as parameter. The language is complete and flexible enough in order to handle any DICOM message.

The present invention can be applied to different fields in the creation and development of medical equipment and systems. Among other things, these are DICOM editors, acquisition simulators and software-based agents or proxies that require DICOM messages for communication or conversion between systems having different manufacturers or systems of different generations, old systems.

Inventively, the readiness of DICOM implementations in medical devices can be tested in an especially easy way, since the separation of the compulsion and the structure makes it possible to generate DICOM messages that are arbitrarily complex or are even partially invalid.

It should also be noted that the present invention requires only two ways of presenting values:

1. The normal way employs strings.

This is compatible with common text editors and is the most common denominator 4 most of all data types defined in DICOM.

2. The indirect way leads the language to read the data values from a case, to be handled a bit stream or any other data value that cannot be simply represented by a string.

Further primitives such as delete and repeat commands are omitted since they can be implemented by using the four basic primitives. Other commands such as debugging or commenting are likewise omitted since they are usually part of an implementation.

Appendix 2 is an example of a waveform described in the DICOM standard in the inventive cdf command language.

Appendix 3 shows an example code that describes how an ASCII representation (CDF) can be converted into a DICOM binary format.

Appendix 1

Abbreviations employed in the specification:

| | |
|---|---|
| CDF | Create Dicom File |
| DICOM | Digital Imaging and Communications in Medicine |
| | DICOM-standard is an industrial standard for the transmission of images and other medical information between computers for enabling digital communication between diagnosis and therapy devices of different manufacturers |
| EPR | Electronic-Patient-Record |
| IE | Information Entities (from DICOM) |
| IOD | Information Object Descriptor (from DICOM) |
| MPPS | Modality Performed Procedure Step |
| PACS | Picture Archival and Communication System |
| RIS | Radiology Information System:<br>Information system for data management within the radiology department that, for example, supports access to the patients, the creation of work lists, reporting, report management, bookkeeping and accounting, etc. |
| SQ | Sequence (from DICOM) |

Commands employed in the specification

| | |
|---|---|
| o | openSQ, |
| c | closeSQ, |
| s | setContentFromString |
| f | setContentFromFile |
| # | commentary line |
| q | end of program |

Appendix 2

\# Hand made Waveform, Final Text version

\#

\# 2000-03-08/Bj

\#

\# Dates for creation are set to 19991231

\# Times for creation are set to 235959

\#

\# Instances = ...113750.CCYYMMDD.HHMMSS.[0-3], 0=Pat 1=Stu 2=Ser 3=WF

\# Ref UIDs  = ...113750.99.99.9999 with ext 0 for instances

\#

\#

\#

\# s (0002,0000) 166 f (0002,0001) .\wf_1_fnltxt.ima.0100.00020001.ob

\# -------------------- media storage SOP Class UID s (0002,0002) 1.2.840.10008.5.1.4.1.1.9.3.1

\# -------------------- media storage SOP Instance UID s (0002,0003) 1.2.840.113750.99991

\# -------------------- transfer syntax s (0002,0010) 1.2.840.10008.1.2.1

\# -------------------- Implementation Class UID s (0002,0012) 1.2.840.113654.2.3.1995.2.8.9 s (0002,0013) MEDCOM_SYNTH

(0002,0102) .\wf_1_fnltxt.ima.0100.00020102.ob

-------------------- SOP Class UID s (0008,0016) 1.2.840.10008.5.1.4.1.1.9.1.1 s (0008,0016) 1.2.840.10008.5.1.4.1.1.9.1.2 s (0008,0016) 1.2.840.10008.5.1.4.1.1.9.1.3 s (0008,0016) 1.2.840.10008.5.1.4.1.1.9.2.1 s (0008,0016) 1.2.840.10008.5.1.4.1.1.9.3.1 s (0008,0016) 1.2.840.10008.5.1.4.1.1.9.4.1 s (0008,0012) 19991231 s (0008,0013) 235959

-------------------- Instance creator, creating device s (0008,0014) 1.2.840.113750.99.12.9002

-------------------- SOP Instance UID s (0008,0018) 1.2.840.113750.19991231.235959.1.1 s (0008,0018) 1.2.840.113750.19991231.235959.1.2 s (0008,0018) 1.2.840.113750.19991231.235959.1.3 s (0008,0018) 1.2.840.113750.19991231.235959.2.1 s (0008,0018) 1.2.840.113750.19991231.235959.3.1 s (0008,0018) 1.2.840.113750.19991231.235959.4.1 s (0008,0020) 19991231 s (0008,0021) 19991231 s (0008,0023) 19991231 s (0008,002A) 19991231235959 s (0008,0030) 235959 s (0008,0031) 235959 s (0008,0033) 235959 s (0008,0050) ACC_NUM

-------------------- Modality s (0008,0060) ECG s (0008,0060) EPS s (0008,0060) HD s (0008,0060) AU s (0008,0060) EPS s (0008,0070) PATMAN SYNTHETIC WAVEFORM LAB s (0008,0080) TEST LABORATORY 1 s (0008,0090) DR^NO s (0008,1030) STUDY_DESCRIPTION s (0008,1048) OVERALL_RESPONSIBLE_PHYSICIAN s (0008,1060) STUDY_READING_PHYSICIAN s (0008,1080) ADMITTING_DIAGNOSIS

O (0008,1199)

-------------------- Referenced SOP Class UID s (0008,1150) 1.2.840.10008.5.1.4.1.1.9.3.1

-------------------- Referenced SOP Instance UID s (0008,1155) 1.2.840.113750.99.99.9999.0

C (0008,1199)

s (0010,0010) NIEMANDSON^NIEMAND^SYNTHESIZED s (0010,0020) 4713 s (0010,0030) 19701231 s (0010,0032) 235959 s (0010,0040) O s (0010,1000) ITS_OTHER_ID s (0010,1001) ITS_OTHER_NAME s (0010,1010) 030Y s (0010,1020) 1.80 s (0010,1030) 75 s (0010,2160) MARSIAN RACE s (0010,2180) OCCUPATION s (0010,21B0) ADDITIONAL PATIENT'S HISTORY s (0010,4000) THE PATIENT IS SYNTHESIZED s (0018,1061) GENEREQUIP1 s (0018,106A) EXTERNAL

-------------------- WF chan id for sync s (0018,106C) 1 s (0018,1800) N s (0018,1801) SYNCSOURCE1 s (0018,1802) GPS

-------------------- study instance uid s (0020,000D) 1.2.840.113750.19991231.235959.1

-------------------- Series instance uid s (0020,000E) 1.2.840.113750.19991231.235959.2

------------------ equip. gen. study identifier s (0020,0010) GENEREQUIP1

------------------ Series Number s (0020,0011) 1

------------------ Waveform number s (0020,0013) 1 s (0020,0060) R

------------------ Sync Inst. FrameofRefUID s (0020,0200) 1.2.840.113750.99.99.9999.0

O (0040,B020)

O (0040,08EA)

s (0008,0100) CODEVALUE s (0008,0102) CODESCHEME s (0008,0103) SCHEMEVERSION s (0008,0104) CODEMEANING s (0008,0105) MAPRESOURCE s (0008,0106) 19991231235959 s (0008,0107) 19991231235959 s (0008,010B) CODESETEXTFLAG s (0008,010C) 1.2.840.113750.99.99.9999 s (0008,010D) 1.2.840.113750.99.99.9999 s (0008,010F) 9999

C (0040,08EA)

O (0040,A043)

s (0008,0100) CODEVALUE s (0008,0102) CODESCHEME s (0008,0103) SCHEMEVERSION s (0008,0104) CODEMEANING s (0008,0105) MAPRESOURCE s (0008,0106) 19991231235959 s (0008,0107) 19991231235959 s (0008,010B) CODESETEXTFLAG s (0008,010C) 1.2.840.113750.99.99.9999 s (0008,010D) 1.2.840.113750.99.99.9999 s (0008,010F) 9999

O (0040,A195)

s (0008,0100) CODEVALUE s (0008,0102) CODESCHEME s (0008,0103) SCHEMEVERSION s (0008,0104) CODEMEANING s (0008,0105) MAPRESOURCE s (0008,0106) 19991231235959 s (0008,0107) 19991231235959 s (0008,010B) CODESETEXTFLAG s (0008,010C) 1.2.840.113750.99.99.9999 s (0008,010D) 1.2.840.113750.99.99.9999 s (0008,010F) 9999

C (0040,A195)

C (0040,A043)

s (0040,A0B0) 1 s (0040,A138) 300 s (0040,A13A) 19991231235959

O (0040,A168)

s (0008,0100) CODEVALUE s (0008,0102) CODESCHEME s (0008,0103) SCHEMEVERSION s (0008,0104) CODEMEANING s (0008,0105) MAPRESOURCE s (0008,0106) 19991231235959 s (0008,0107) 19991231235959 s (0008,010B) CODESETEXTFLAG s (0008,010C) 1.2.840.113750.99.99.9999 s (0008,010D) 1.2.840.113750.99.99.9999 s (0008,010F) 9999

O (0040,A195)

s (0008,0100) CODEVALUE s (0008,0102) CODESCHEME s (0008,0103) SCHEMEVERSION s (0008,0104) CODEMEANING s (0008,0105) MAPRESOURCE s (0008,0106) 19991231235959 s (0008,0107) 19991231235959 s (0008,010B) CODESETEXTFLAG s (0008,010C) 1.2.840.113750.99.99.9999 s (0008,010D) 1.2.840.113750.99.99.9999 s (0008,010F) 9999

C (0040,A195)

C (0040,A168)

s (0040,A180) 1

O (0040,A195)

s (0008,0100) CODEVALUE s (0008,0102) CODESCHEME s (0008,0103) SCHEMEVERSION s (0008,0104) CODEMEANING s (0008,0105) MAPRESOURCE s (0008,0106) 19991231235959 s (0008,0107) 19991231235959 s (0008,010B) CODESETEXTFLAG s (0008,010C) 1.2.840.113750.99.99.9999 s (0008,010D) 1.2.840.113750.99.99.9999 s (0008,010F) 9999

C (0040,A195)

C (0040,B020)

O (0040,0555)

O (0040,08EA)

s (0008,0100) CODEVALUE s (0008,0102) CODESCHEME s (0008,0103) SCHEMEVERSION s (0008,0104) CODEMEANING s (0008,0105) MAPRESOURCE s (0008,0106) 19991231235959 s (0008,0107) 19991231235959 s (0008,010B) CODESETEXTFLAG s (0008,010C) 1.2.840.113750.99.99.9999 s (0008,010D) 1.2.840.113750.99.99.9999 s (0008,010F) 9999

C (0040,08EA)

O (0040,A043)

s (0008,0100) CODEVALUE s (0008,0102) CODESCHEME s (0008,0103) SCHEMEVERSION s (0008,0104) CODEMEANING s (0008,0105) MAPRESOURCE s (0008,0106) 19991231235959 s (0008,0107) 19991231235959 s (0008,010B) CODESETEXTFLAG s (0008,010C) 1.2.840.113750.99.99.9999 s (0008,010D) 1.2.840.113750.99.99.9999 s (0008,010F) 9999

C (0040,A043)

```
s (0040,A121) 19991231
s (0040,A122) 235959
s (0040,A123) NIEMANDSON^NIEMAND^SYNTHESIZED
s (0040,A136) 1
O (0040,A168)
    s (0008,0100) CODEVALUE
    s (0008,0102) CODESCHEME
    s (0008,0103) SCHEMEVERSION
    s (0008,0104) CODEMEANING
    s (0008,0105) MAPRESOURCE
    s (0008,0106) 19991231235959
    s (0008,0107) 19991231235959
    s (0008,010B) CODESETEXTFLAG
    s (0008,010C) 1.2.840.113750.99.99.9999
    s (0008,010D) 1.2.840.113750.99.99.9999
    s (0008,010F) 9999
C (0040,A168)
    s (0040,0556) FREE TEXT HERE
C (0040,0555)
s (0040,0556) FREE TEXT HERE
O (5400,0100)
    s (0018,1068) 500
    s (0018,1069) 600
    s (0018,106E) 1
``` s (003A,0004) ORIGINAL s (003A,0005) 1 s (003A,0010) 1000 s (003A,001A) 20000 s (003A,0020) MUX_GRP_LBL

O (003A,0200)

s (003A,0202) 1 s (003A,0203) TXT_LBL s (003A,0205) UNCALIBRATED

O (003A,0208)

s (0008,0100) CODEVALUE s (0008,0102) CODESCHEME s (0008,0103) SCHEMEVERSION s (0008,0104) CODEMEANING s (0008,0105) MAPRESOURCE s (0008,0106) 19991231235959 s (0008,0107) 19991231235959 s (0008,010B) CODESETEXTFLAG s (0008,010C) 1.2.840.113750.99.99.9999 s (0008,010D) 1.2.840.113750.99.99.9999 s (0008,010F) 9999

C (003A,0208)

O (003A,0209)

s (0008,0100) CODEVALUE s (0008,0102) CODESCHEME s (0008,0103) SCHEMEVERSION s (0008,0104) CODEMEANING s (0008,0105) MAPRESOURCE s (0008,0106) 19991231235959 s (0008,0107) 19991231235959 s (0008,010B) CODESETEXTFLAG s (0008,010C) 1.2.840.113750.99.99.9999 s (0008,010D) 1.2.840.113750.99.99.9999 s (0008,010F) 9999

C (003A,0209)

O (003A,020A)

s (0008,1150) 1.2.840.113750.99.99.9999 s (0008,1155) 1.2.840.113750.99.99.9999 s (0040,A0B0) 1 s (0040,A0B0) 1

C (003A,020A)

s (003A,020C) ADDITIONAL DESCR TEXT s (003A,0210) 32

O (003A,0211)

s (0008,0100) CODEVALUE s (0008,0102) CODESCHEME s (0008,0103) SCHEMEVERSION s (0008,0104) CODEMEANING s (0008,0105) MAPRESOURCE s (0008,0106) 19991231235959 s (0008,0107) 19991231235959 s (0008,010B) CODESETEXTFLAG s (0008,010C) 1.2.840.113750.99.99.9999 s (0008,010D) 1.2.840.113750.99.99.9999 s (0008,010F) 9999

C (003A,0211)

s (003A,0212) 12 s (003A,0213) 13 s (003A,0214) 14 s (003A,0215) 15 s (003A,0218) 18 s (003A,021A) 16 s (003A,0220) 220 s (003A,0221) 221 s (003A,0222) 222 s (003A,0223) 223

C (003A,0200)

s (5400,1004) 16 s (5400,1006) US f (5400,1010) .\wf_1_fnltxt.ima.0110.54001010.ow

C (5400,0100)

q

Appendix 3

```
// Schematic example code for a tool converting from an ASCII based file
// using the minimal language (set-content-from-string,
//                             set-content-from-file,
//                             open-item,
//                             close-item)
//
// with some cosmetic extensions for debugging and comments.
// The toolkit refers to some software toolkit/library which can build
// the binary DICOM stream via a C-language API.

// ------------------------------------------------ include <stdio.h>
include <string.h>

// include some-dicom-toolkit-header-files
// for dicom stream build and dicom constrains checking

// ------------------------------------------------

// Globals
#define BIGSTRSIZE 1000
#define BIGPNAMESIZE 500
```

```
define BUFFERSIZE 1024*1024*10 define VRSIZE 3 define TOOLKIT_SET_FROM_STR 's' define TOOLKIT_SET_FROM_FUN 'f' define OPEN_ITEM 'O' define CLOSE_ITEM 'C' define TOOLKIT_DUMP 'D' define DEBUGTOGGLE '!' define COMMENT_BEGIN '#' define QUIT 'q'

// Toolkit data structures should be added here char    appName[10] = "foobar";

char*   fileName;

int lineNo = 0; // line number in input command file typedef struct line_t
{
  int cmd;
  unsigned long tag;
  char value[BIGSTRSIZE];
```

```
  unsigned long slot1;          // DICOM group value
  char slot2[BIGPNAMESIZE];     // DICOM private tag: OwnerCode
  unsigned long slot3;          // DICOM element value or DICOM private tag:
                                   ElementByte
  char slot4[VRSIZE];           // DICOM private tag: value representation } line_t;

line_t line;

char callbackdata = 0x1;

// Stack for message id
#define STACKMAXVAL 10000
int messageId_sp=0;
int messageId_val[STACKMAXVAL];

// -----------------------------------------------
// Functions void pushmessageId(int v){
  if (messageId_sp < STACKMAXVAL)
    messageId_val[messageId_sp++] = v;
  else
```

```c
      fprintf(stderr, "Schematic-example-code at cmdline %d: Stack overflow\n",lineNo);
} int popmessageId(void){
  if (messageId_sp>0)
    return messageId_val[--messageId_sp];
  else {
    fprintf(stderr, "Schematic-example-code at cmdline %d: Stack underflow\n",lineNo);
    return 0;
  }
} void ErrExit(char * errMessage, int errNum)
{
  if (errNum == OK) {
    fprintf(stderr, "Schematic-example-code at cmdline %d: %s\n", lineNo, errMessage);
  } else {
    fprintf(stderr, "Schematic-example-code at cmdline %d: %s  with TOOLKIT error %s\n", lineNo, errMessage, Error_Message( (STATUS) errNum));
  }
  status = Release_Application( &appID);
  exit(-1);
}
```

```
static STATUS simpleCallBack (
        int             messageID,
        unsigned long   tag,
        int             firstCall,
        void*           userInfo,
        int*            dataLen,
        void**          dataBuffer,
        int*            isLast)
{
    static char   buffer[BUFFERSIZE];
    size_t        byte_pos;
    FILE *stream;
    char errMessage[100];
    int ch;

*isLast = 1;

if( (stream = fopen( line.value, "rb" )) == NULL ) {
      sprintf( errMessage,"Failed to open file: '%s'\n", line.value );
      ErrExit(errMessage,OK);
    } byte_pos = 0;
    ch = fgetc( stream );
```

```
while ( feof( stream ) == 0 ) { buffer[byte_pos] = ch;

ch = fgetc( stream );

byte_pos++;

}
// byte_pos points one ahead of last filled pos in buffer and equals number of bytes if( fclose( stream ) ) { sprintf( errMessage,"Failed to close file: '%s'\n", line.value );

ErrExit(errMessage,OK);

}

// if odd number of bytes report error
if ((byte_pos % 2) == 1) {

ErrExit("Odd number of bytes read.\n",OK);

}

*dataBuffer = buffer;

*dataLen = (int)byte_pos;

return OK;

}

VR str2vr(char * str)
```

{ if ((str[0] == 'A') && (str[1] == 'E')){return AE;} if ((str[0] == 'A') && (str[1] == 'S')){return AS;} if ((str[0] == 'C') && (str[1] == 'S')){return CS;} if ((str[0] == 'D') && (str[1] == 'A')){return DA;} if ((str[0] == 'D') && (str[1] == 'S')){return DS;} if ((str[0] == 'D') && (str[1] == 'T')){return DT;} if ((str[0] == 'I') && (str[1] == 'S')){return IS;} if ((str[0] == 'L') && (str[1] == 'O')){return LO;} if ((str[0] == 'L') && (str[1] == 'T')){return LT;} if ((str[0] == 'P') && (str[1] == 'N')){return PN;} if ((str[0] == 'S') && (str[1] == 'H')){return SH;} if ((str[0] == 'S') && (str[1] == 'T')){return ST;} if ((str[0] == 'T') && (str[1] == 'M')){return TM;} if ((str[0] == 'U') && (str[1] == 'T')){return UT;} if ((str[0] == 'U') && (str[1] == 'I')){return UI;} if ((str[0] == 'S') && (str[1] == 'S')){return SS;} if ((str[0] == 'U') && (str[1] == 'S')){return US;} if ((str[0] == 'A') && (str[1] == 'T')){return AT;} if ((str[0] == 'S') && (str[1] == 'L')){return SL;} if ((str[0] == 'U') && (str[1] == 'L')){return UL;} if ((str[0] == 'F') && (str[1] == 'L')){return FL;} if ((str[0] == 'F') && (str[1] == 'D')){return FD;}

```c
if ((str[0] == 'O') && (str[1] == 'B')){return OB;}
if ((str[0] == 'O') && (str[1] == 'W')){return OW;}
if ((str[0] == 'O') && (str[1] == 'L')){return OL;}
if ((str[0] == 'S') && (str[1] == 'Q')){return SQ;} return UNKNOWN_VR;
} void trim_rest_of_line(void)
{
  int c;

c = getchar();
  while (c != '\n') {
    if (c == EOF) {
    return;
    }
    c = getchar();
  }
} void trim(void)
{
```

```
    int c;

c = getchar();
    while ((c == ' ') ||
      (c == '\t')) {
      c = getchar();
    }
    ungetc(c,stdin);
} int parseLine(line_t *line)
{
    enum{CMD, TAG, VALUE} state = CMD;
    int c,i;
    char tagAsStr[BIGSTRSIZE];

// clear return data line->cmd = 0;
    line->tag = 0;

for(i=0; i < BIGSTRSIZE; i++) {
      line->value[i] = '\0';
    }
```

```
line->slot1 = 0;

line->slot3 = 0;

for(i=0; i < BIGPNAMESIZE; i++) { line->slot2[i] = '\0';

} for(i=0; i < VRSIZE; i++) { line->slot4[i] = '\0';

} for(i=0; i<BIGSTRSIZE; i++) { tagAsStr[i] = '\0';

} trim();

// get the command c = getchar();

line->cmd = c;

if ((c == EOF) || (c == QUIT)) {
```

```
    return EOF;
} if (c == COMMENT_BEGIN) {
  trim_rest_of_line();
  return COMMENT_BEGIN;
} if (c == TOOLKIT_DUMP) {
  trim_rest_of_line();
  return TOOLKIT_DUMP;
} if (c == DEBUGTOGGLE) {
  trim_rest_of_line();
  return DEBUGTOGGLE;
} if (!((c == TOOLKIT_SET_FROM_STR) ||
   (c == TOOLKIT_SET_FROM_FUN) ||
   (c == TOOLKIT_DUMP) ||
   (c == OPEN_ITEM) ||
   (c == CLOSE_ITEM))) {
```

```
    ErrExit("Failed to parse line, unexpected cmd\n",OK);
} trim();

// get the first slot of the tag.
// Tag format:
//     (0008,0090)
//     (0009,FOOBAR INCORP CM VA0  CMS,11)

if ((c = getchar()) != '(') {
    ErrExit("Failed to parse line, tag must begin with a parantesis\n",OK);
} for(i=0; i<4; i++) {
  c = getchar();
  if (((c >= '0') && (c <= '9')) ||
  ((c >= 'A') && (c <= 'F')))
   {
tagAsStr[i] = c;
   } else
   {
ErrExit("Failed to parse line, invalid tag\n",OK);
   }
```

```
} if (sscanf(tagAsStr,"%X",&line->slot1) != 1) {

ErrExit("sscanf failed\n",OK);

} for(i=0; i<BIGSTRSIZE; i++) { tagAsStr[i] = '\0';

} if ((c = getchar()) != ',') {

ErrExit("Failed to parse line, missing comma after group element in tag\n",OK);

}

// get the second slot

// if a comma follows its private if endparantesis it's a normal tag, else error c = getchar();

i = 0;

while (!((c == ',') ||

(c == ')'))) { if ((c == '\n') ||

(c == EOF)) {
```

```
        ErrExit("Failed to parse line, unexpected end in tag\n",OK);
    } tagAsStr[i++] = c;

c = getchar();

} if (c == ')') { // nonprivate tag for(i=0; i<4; i++) { if (!(((tagAsStr[i] >= '0') && (tagAsStr[i] <= '9')) ||

((tagAsStr[i] >= 'A') && (tagAsStr[i] <= 'F')))) {

ErrExit("Failed to parse line, invalid hex value in second part of nonprivate tag\n",OK);

}
    } if (sscanf(tagAsStr,"%X",&line->slot3) != 1) {

ErrExit("sscanf failed, expected hex as second and last part of tag\n",OK);

}

} else { // private tag
```

```
strcpy(line->slot2,tagAsStr);

if (c != ',') {
  ErrExit("Failed to parse line, comma after slot2 missing in private tag\n",OK);
} for(i=0; i<BIGSTRSIZE; i++) {
  tagAsStr[i] = '\0';
}

// slot3
c = getchar();
i = 0;
while (c != ',') { if ((c == '\n') ||
    (c == EOF)) {
  ErrExit("Failed to parse line, unexpected end in slot3 in private tag\n",OK);
  } tagAsStr[i++] = c;
  c = getchar();
}
```

```
// slot4 line->slot4[0] = getchar();

line->slot4[1] = getchar();

if ((c = getchar()) != ')') {

ErrExit("Failed to parse line, missing ending parantesis in private tag\n",OK);

} if (sscanf(tagAsStr,"%X",&line->slot3) != 1) {

ErrExit("sscanf failed\n",OK);

}
} if ((line->cmd == TOOLKIT_SET_FROM_STR) || (line->cmd == TOOLKIT_SET_FROM_FUN))
{ c = getchar();
  if (!((c == ' ') || (c == '\t')))
  {
    ErrExit("Failed to parse line, delimiter before value not space or tab\n",OK);
  }
}
else
{
```

```
    trim();
}

// get the value
c = getchar();
i = 0;
while (!((c == EOF) ||
    (c == '\n'))) {
    line->value[i++] = c;
    c = getchar();
} return c; // EOF or '\n'
} int
main(int argc, char * argv[])
{
  int outer_messageId;
  bool debugging = FALSE;

if (argc != 2)
  {
```

```c
        fprintf(stderr, "\nSchematic-example-code Usage: Schematic-example-code outfile < commands\n\n");

fprintf(stderr, "List of commands:\n\n");

fprintf(stderr, "\t's' for TOOLKIT_SET_FROM_STR \n");

fprintf(stderr, "\t'f' for TOOLKIT_SET_FROM_FUN \n");

fprintf(stderr, "\t'O' for OPEN_ITEM \n");

fprintf(stderr, "\t'C' for CLOSE_ITEM \n");

fprintf(stderr, "\t'D' for TOOLKIT_DUMP \n");

fprintf(stderr, "\t'!' for DEBUGTOGGLE \n");

fprintf(stderr, "\t'#' for COMMENT_BEGIN \n");

fprintf(stderr, "\t'q' for QUIT \n");

return -1;

} fileName = argv[1];

// init the toolkit code here
    // ...

// main loop
    while (parseLine(&line) != EOF) {
```

```
lineNo++;

if ((line.cmd == QUIT) ||
(line.cmd == COMMENT_BEGIN) ||
(line.cmd == DEBUGTOGGLE) ||
(line.cmd == EOF)) { if (debugging) {
    fprintf(stdout, "Schematic-example-code at cmdline %d: parsed cmd = \"%c\" OK!\n", lineNo, line.cmd);
  }

} else { if (line.slot2[0] == '\0') { if (debugging) {
      fprintf(stdout, "Schematic-example-code at cmdline %d: parsed cmd = \"%c\" tag = (%4X,%4X) value \"%s\" OK!\n",
        lineNo,line.cmd,line.slot1,line.slot3,line.value);
    } line.tag = (line.slot1 << 16) + line.slot3;
```

```
    } else { if (debugging) { fprintf(stdout, "Schematic-example-code at cmdline %d: parsed cmd = \"%c\" tag = (%4X,%s,%4X,%s) value \"%s\" OK!\n", lineNo,line.cmd,line.slot1,line.slot2, line.slot3, line.slot4,line.value,lineNo);

}
  }
  } switch (line.cmd) { case TOOLKIT_SET_FROM_STR:

if (line.slot2[0] == '\0')  // standard tag
    {
      if (strcmp(line.value, "") == 0)
      {
        status = Toolkit_Set_Next_Value_To_NULL(messageId, line.tag);
        if (status == INCOMPATIBLE_VR)
        {
          status = Toolkit_Set_Next_Value_From_String (messageId, line.tag, "");
        }
      }
```

```
        else
        {
        status = Toolkit_Set_Next_Value_From_String(messageId, line.tag, line.value);
        }
        if ((status != OK) && (status != INVALID_CHARS_IN_VALUE) && (status != INVALID_VALUE_FOR_VR))
        ErrExit("Toolkit_Set_Next_Value_From_String", status);

}
    else                // private tag
    { unsigned long aValLength;
    status = Get_privateValue_Length(messageId,
            line.slot2,
            (unsigned short) line.slot1,
            (unsigned char) line.slot3,
            1,
            &aValLength);
    if ((status == NULL_VALUE) || (status == EMPTY_VALUE))
    {
      status = OK;
    }
```

```
if (!((status == OK) ||
    (status == INVALID_PRIVATE_CODE) ||
    (status == INVALID_TAG))) {
  ErrExit("Get_privateValue_Length", status);
}

// CASE no owner element; no data element:
if (status == INVALID_PRIVATE_CODE) {
  status = Add_Private_Block(messageId,line.slot2,(unsigned char)line.slot1);
  if (status == OK) { status = Add_Private_Attribute(messageId,line.slot2,
            (unsigned short)line.slot1,
            (unsigned char)line.slot3,
            str2vr(line.slot4));
    if (status != OK) {
      ErrExit("Add_Private_Attribute failed", status);
    }
  } else {
    ErrExit("Add_Private_Block failed", status);
  }
} else if (status == INVALID_TAG) {

// CASE owner element exist; no data element: do 2.
```

```c
        status = Add_Private_Attribute(messageId,line.slot2, (unsigned short)line.slot1, (unsigned char)line.slot3, str2vr(line.slot4));

if (status != OK) {

ErrExit("Add_Private_Attribute\n", status);

}

} else if (status == OK) {

// CASE owner element exist; data element exist: do 3.

status = Toolkit_Set_privateValue_Representation(messageId,line.slot2, (unsigned short)line.slot1, (unsigned char)line.slot3, str2vr(line.slot4));

if (!((status == OK) ||

(status == VR_ALREADY_VALID))) {

ErrExit("Toolkit_Set_privateValue_Representation", status);

}

} else {

ErrExit("Other error while doing private attribute", status);

}

// We have possibly built a private structure, now set the private value if (strcmp(line.value, "") == 0)
```

```
        {
     status = Toolkit_Set_Next_privateValue_To_NULL(messageId,
                line.slot2,
                (unsigned short)line.slot1,
                (unsigned char)line.slot3);
      if (status == INCOMPATIBLE_VR)
      {
     status = Toolkit_Set_Next_privateValue_From_String (messageId,
                line.slot2,
                (unsigned short)line.slot1,
                (unsigned char)line.slot3,
                "");
      }
    }
     else
     {
     status = Toolkit_Set_Next_privateValue_From_String (messageId,
                line.slot2,
                (unsigned short)line.slot1,
                (unsigned char)line.slot3,
                line.value);
     }
     if ((status != OK) && (status != INVALID_CHARS_IN_VALUE) && (status != INVALID_VALUE_FOR_VR))
```

-47-

```
        {
    ErrExit("Toolkit_Set_Next_privateValue_From_String", status);
        }
    }
    break;

case TOOLKIT_SET_FROM_FUN:
    if (line.slot2[0] == '\0') { // standard tag status   = Toolkit_Set_Value_From_Function(messageId, line.tag, NULL, simpleCallBack);
        if (status != OK)
            ErrExit("Toolkit_Set_Value_From_Function", status);

} else { unsigned long aValLength;
        status = Get_privateValue_Length(messageId,
                line.slot2,
                (unsigned short) line.slot1,
                (unsigned char) line.slot3,
                1,
                &aValLength);
```

```
if (!((status == OK) ||
    (status == INVALID_PRIVATE_CODE) ||
    (status == INVALID_TAG))) {
  ErrExit("Get_privateValue_Length", status);
}

// CASE no owner element; no data element:
if (status == INVALID_PRIVATE_CODE) {
  status = Add_Private_Block(messageId,line.slot2,(unsigned char)line.slot1);
  if (status == OK) { status = Add_Private_Attribute(messageId,line.slot2,
        (unsigned short)line.slot1,
        (unsigned char)line.slot3,
        str2vr(line.slot4));
    if (status != OK) {
      ErrExit("Add_Private_Attribute failed", status);
    }
  } else {
    ErrExit("Add_Private_Block failed", status);
  }
} else if (status == INVALID_TAG) {

// CASE owner element exist; no data element: do 2.
```

```
status = Add_Private_Attribute(messageId,line.slot2,
            (unsigned short)line.slot1,
            (unsigned char)line.slot3,
            str2vr(line.slot4));
if (status != OK) {
  ErrExit("Add_Private_Attribute\n", status);
}
} else if (status == OK) {

// CASE owner element exist; data element exist: do 3.

status = Toolkit_Set_privateValue_Representation(messageId,line.slot2,
            (unsigned short)line.slot1,
            (unsigned char)line.slot3,
            str2vr(line.slot4));
if (!((status == OK) ||
    (status == VR_ALREADY_VALID))) {
  ErrExit("Toolkit_Set_privateValue_Representation", status);
}
} else {
  ErrExit("Other error while doing private attribute", status);
}
// We have possibly built a private structure, now set the private value
if ((status = Toolkit_Set_privateValue_From_Function (messageId,
```

```
                        line.slot2,
                        (unsigned short)line.slot1,
                        (unsigned char)line.slot3,
                        NULL,
                        simpleCallBack)) != OK) {
            ErrExit("Toolkit_Set_privateValue_From_Function", status);
        }
    }
    break;

case CLOSE_ITEM:
        outer_messageId = popmessageId();
        Toolkit_Set_Next_Value_From_Int(outer_messageId, line.tag, messageId);
        messageId = outer_messageId;
        if (status != OK)
            ErrExit("Toolkit_Set_Value_from_int", status);
        break;

case TOOLKIT_DUMP:
        List_File(messageId, NULL);
        if (status != OK)
            ErrExit("List_File", status);
        break;
```

```
case OPEN_ITEM:

pushmessageId(messageId);

status = Open_Item(&messageId, line.value);

if (status != OK)
ErrExit("Open_Item", status);

break;

case COMMENT_BEGIN:

// do nothing for comments break;

case DEBUGTOGGLE:

if (debugging) { debugging = FALSE;

} else { debugging = TRUE;

} break;

default:

fprintf(stderr, "Schematic-example-code at cmdline %d: \"%c\": ",lineNo,line.cmd);

ErrExit("Unexpected value",OK);

break;
}
```

```
} if (debugging) { fprintf(stdout, "Schematic-example-code: Writing dicom output to: %s\n", fileName);

} long aStatus = UNDEFINED;

TransferSyntax aSyntax;

const int aBufferSize = 128;

char aBuffer[aBufferSize];

status = Get_Value_To_String(messageId, 0x00020010, aBufferSize, aBuffer);

if (status == OK)

{ aSyntax.setFromUidString(aBuffer);

} else

{ status = File_To_Message(messageId);

if (status != OK)

{

ErrExit("File_To_Message", status);

} aSyntax.setFromString("STREAM_IMPLICIT_LITTLE_ENDIAN");
```

}

```
aStatus = encodeDicomList(messageId, fileName, aSyntax);

if (aStatus != SUCCESS)

{ fprintf(stderr, "Schematic-example-code at cmdline %d: %s\n", lineNo, "encodeDicomList() failed");

} return 0;

} // main
```

Although modifications and changes may be suggested by those skilled in the art, it is in the intention of the inventor to embody within the patent warranted hereon all changes and modifications as reasonably and properly come within the scope of his contribution to the art.

I claim as my invention:

1. A method for processing objects of a standardized communication protocol for image and data exchange between a plurality of devices connected via a communication network, said devices including processing devices wherein said objects are processed, comprising the steps of:

converting DICOM objects, each having a tag with a defined reference tag value, into a pure text file via a conversion routine and also, in said conversion routine, generating, for at least some of said tag values, a binary file associated with a position of the compressed DICOM object within the pure text file, said binary file containing the converted DICOM object referenced by the tag;

processing said pure text file with a generic minimalistic type class-dependent command language; and reconverting said pure text file into the DICOM objects by substituting respective binary files for their placeholders associated tag reference in the pure text file.

2. A method as claimed in claim 1 comprising, in said conversion routine, employing a type class for said tags selected from the group consisting of byte, word and long types, and floating types.

3. A method as claimed in claim 2 comprising, in said conversion routine, allowing for augmentation of said type classes without altering said pure text file.

4. A method as claimed in claim 2 comprising, in said conversion routine, using a minimal command language specification to reconvert said pure text file into said DICOM objects.

5. A method as claimed in claim 4 comprising employing, in said minimal command language, at least one command selected from the group consisting of a command setting a value from a string representation, a command setting a value from a binary reference, a command that opens a sequence of said tags, a command that closes a last-opened sequence of said tags, and a command ending a command sequence.

6. A method as claimed in claim 2 comprising, in said conversion subroutine, employing a minimal command language specification to create a complete pure text file from a complete DICOM object.

* * * * *